US009713605B2

(12) United States Patent
Chia et al.

(10) Patent No.: US 9,713,605 B2
(45) Date of Patent: Jul. 25, 2017

(54) **AMELIORATIVE OR PREVENTIVE EFFECT OF *ANTRODIA CINNAMOMEA* IN ARTHRITIS, CARTILAGE DESTRUCTION, OR CHONDROCYTE DEATH**

(71) Applicants: Wei-Tso Chia, Hsinchu (TW); Chia-Chin Sheu, Taoyuan County (TW)

(72) Inventors: Wei-Tso Chia, Hsinchu (TW); Chia-Chin Sheu, Taoyuan County (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 1127 days.

(21) Appl. No.: 13/681,336

(22) Filed: Nov. 19, 2012

(65) Prior Publication Data

US 2013/0129772 A1 May 23, 2013

Related U.S. Application Data

(60) Provisional application No. 61/561,355, filed on Nov. 18, 2011.

(51) Int. Cl.

| | | |
|---|---|---|
| *A01N 65/00* | (2009.01) | |
| *A61K 31/4015* | (2006.01) | |
| *H01S 3/02* | (2006.01) | |
| *A61K 31/341* | (2006.01) | |
| *H01S 3/086* | (2006.01) | |
| *H01S 3/0941* | (2006.01) | |
| *H01S 3/109* | (2006.01) | |
| *H01S 3/16* | (2006.01) | |
| *H01S 3/06* | (2006.01) | |

(52) U.S. Cl.
CPC ........ *A61K 31/4015* (2013.01); *A61K 31/341* (2013.01); *H01S 3/02* (2013.01); *H01S 3/025* (2013.01); *H01S 3/0604* (2013.01); *H01S 3/086* (2013.01); *H01S 3/09415* (2013.01); *H01S 3/109* (2013.01); *H01S 3/1611* (2013.01); *H01S 3/1673* (2013.01)

(58) Field of Classification Search
CPC .................................................... A61K 36/00
USPC ....................................................... 424/725
See application file for complete search history.

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 7,109,232 B2 | 9/2006 | Hattori et al. |
| 7,732,482 B2 | 6/2010 | Hattori et al. |

OTHER PUBLICATIONS

Hunter, "Risk Stratification for Knee Osteoarthritis Progression: A Narrative Review" Osteoarthritis and Cartilage, May 3, 2009, pp. 1402-1407, vol. 17.
Haywood, et al., "Inflammation and Angiogenesis in Osteoarthritis", Arthritis & Rheumatism, Aug. 2003, pp. 2173-2177, vol. 48, No. 8.
Chia, et al., "Experimental Osteoarthritis induced by Surgical Realignment of the Patella in BALB/c Mice", The Journal of Bone and Joint Surgery, Dec. 2010, pp. 1710-1717, 92(12).
Han, et al., "Protective Effects of a Neutral Polysaccharide Isolated from the Mycelium of Antrodia Cinnamomea on Propionibacterium Acnes and Lipopolysaccharide Induced Hepatic Injury in Mice", Chem. Pharm. Bull., Apr. 2006, pp. 496-500, vol. 54, No. 4.
Firestein, "Evolving Concepts of Rheumatoid Arthritis", Nature, May 15, 2003, pp. 356-361, vol. 423.
Chia, et al., "IL-1β in Irrigation Fluid and mRNA Expression in Synovial Tissue of the Knee Joint as Therapeutic Markers of Inflammation in Collagen Antibody-Induced Arthritis", Disease Markers, 2009, pp. 1-7, 26(1).
Chia, et al., "MMP-9 mRNA as a Therapeutic Marker in Acute and Chronic Stages of Arthritis Induced by Type II Collagen Antibody", J Formos Med Assoc., Mar. 2008, pp. 245-252, vol. 107, No. 3.
Terato, et al., "Induction of Arthritis with Monoclonal Antibodies to Collagen", The Journal of Immunology, Apr. 1, 1992, pp. 2103-2108, vol. 148, No. 7.
Nandakumar, et al., "Collagen Type II (CII)-Specific Antibodies Induce Arthritis in the Absence of T or B cells but the Arthritis Progression is Enhanced by CII-Reactive T cells", Arthritis Res Ther, Sep. 23, 2004, pp. R544-R550.
Chia, et al., "A Noncontact Footpad Thickness Assay to Evaluate Rheumatoid Disease", Rheumatol Int, Feb. 2010, pp. 547-550, vol. 30.
Doherty M. "Risk Factors for Progresssion of Knee Osteoarthritis", The Lancet, Sep. 8, 2011, pp. 775-776, vol. 358.

*Primary Examiner* — Michael Meller
(74) *Attorney, Agent, or Firm* — Muncy, Geissler, Olds & Lowe, P.C.

(57) ABSTRACT

The present invention relates to a method of preventing or ameliorating the symptoms of arthritis or preventing or ameliorating cartilage destruction or chondrocyte death in a subject suffered from arthritis, comprising administrating the subject an effective amount of an active component selected from a compound, a mixture, and a mycelium prepared from *Antrodia cinnamomea*.

3 Claims, 14 Drawing Sheets
(7 of 14 Drawing Sheet(s) Filed in Color)

Normal cartilage, score = 0, HE stain, 40X

Normal cartilage, score = 0, HE stain, 200X

Score = 1, HE stain, 100X, cartilage destruction area < 1/3

Score = 2, HE stain, 100X, cartilage destruction area between 1/3 and 2/3

Score = 3, HE stain, 100X, cartilage destruction area > 2/3

Normal chondrocyte, score = 0, HE stain, 40X

Score = 1, HE stain, 100X, chondrocyte death area < 1/3

Score = 1, HE stain, 200X, chondrocyte death area < 1/3

Score = 2, HE stain, 200X, chondrocyte death area between 1/3 and 2/3

Score = 3, HE stain, 100X, chondrocyte death area > 2/3

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Forward primer for IL-1beta

<400> SEQUENCE: 1

```
ccagcaggtt atcatcatca tcc                                    23

<210> SEQ ID NO 2
<211> LENGTH: 19
<212> TYPE: DNA
<213> ORGANISM: Artificial Sequence
<220> FEATURE:
<223> OTHER INFORMATION: Reverse primer for IL-1beta

<400> SEQUENCE: 2
ctcgcagcag cacatcaac                                         19

<210> SEQ ID NO 3
<211> LENGTH: 22
<212> TYPE: DNA
<213> ORGANISM: Artificial Sequence
<220> FEATURE:
<223> OTHER INFORMATION: Forward primer for GAPDH

<400> SEQUENCE: 3
tggcaaagtg gagattgttg cc                                     22

<210> SEQ ID NO 4
<211> LENGTH: 21
<212> TYPE: DNA
<213> ORGANISM: Artificial Sequence
<220> FEATURE:
<223> OTHER INFORMATION: Reverse primer for GAPDH

<400> SEQUENCE: 4
aagatggtga tgggcttccc g                                      21
```

AMELIORATIVE OR PREVENTIVE EFFECT OF *ANTRODIA CINNAMOMEA* IN ARTHRITIS, CARTILAGE DESTRUCTION, OR CHONDROCYTE DEATH

CROSS REFERENCE TO RELATED APPLICATIONS

This application claims priority of U.S. Provisional Application No. 61/561,355 filed on Nov. 18, 2011 under 35 U.S.C. §119(e), the entire contents of which are hereby incorporated by reference.

FIELD OF THE INVENTION

The present invention relates to a method of preventing or ameliorating the symptoms of arthritis in a subject suffered from arthritis and a method of preventing or ameliorating cartilage destruction or chondrocyte death in a subject suffered from arthritis.

BACKGROUND OF THE INVENTION

Rheumatoid arthritis (RA) affects 1% of the adults worldwide. RA's hallmark is leukocyte infiltration of the synovium. This process stimulates the proliferation of apoptosis-resistant fibroblast-like synoviocytes (FLS), leading to pannus formation and joint destruction. Intra-articular expression of cytokines, particularly that of TNF-α and IL-1β, plays key roles in RA pathogenesis.

Osteoarthritis (OA), a slowly progressing disease resulting in articular cartilage fibrillation and loss, is the most common form of arthritis (Hunter, 2009. Risk stratification for knee osteoarthritis progression: a narrative review. Osteoarthritis Cartilage May 3, 2009). Approximately 10-50% of the elderly population is affected by OA, a quarter of whom are severely disabled due to joint symptoms (Haywood et al., 2003. Inflammation and angiogenesis in osteoarthritis. Arthritis Rheum 48:2173-7). The degradative process is believed to be largely mediated by proteases belonging to the matrix metalloproteinase (MMP) class of enzymes. Among these, MMP-1 and MMP-13 are considered to be of particular interest since they directly degrade the components of the cartilage matrix including aggrecan and collagen. Cytokines such as interleukin-1β (IL-1β), are known to strongly induce the production of MMP-1 and MMP-13 by articular joint cells. IL-1β and TNF-α, are widely assumed to play a major role in the pathological process of cartilage degeneration. Previously, a newly designed surgical patella strengthening (SPS)-induced model of OA in BALB/c mice had been setup and OA markers had been established by investigating the relationship between synovial and MMPs (Chia et al., Experimental osteoarthritis induced by surgical realignment of the patella in BALB/c mice. J Bone Joint Surg Br. 2010 December; 92(12):1710-6).

*Antrodia cinnamomea* CHANG TT & WN CHOU (Chinese name, niu-chang-chih or niu-chang-ku; synonym *Antrodia camphorata* WU SH et al.) is a new species of the genus *Antrodia* (family polyporaceae, Aphyllophorales) that is parasitic on the inner cavity of the endemic species *Cinnamomum kanehirai* HAY. This endangered species has been used in Taiwan to treat food, alcohol, and drug intoxication, diarrhea, abdominal pain, hypertension, skin itching and liver cancer as a Chinese folk medicine. The hot water extract of *A. cinnamomea* has hepatoprotective effect. Han et al. showed that the hepatoprotective activity of the extract in mice with *Propionibacterium acnes* (*P. acnes*)—lipopolysaccharide (LPS) induced hepatotoxicity (Han et al., Protective effects of a neutral polysaccharide isolated from the mycelium of *Antrodia cinnamomea* on *Propionibacterium acnes* and lipopolysaccharide induced hepatic injury in mice. Chem Pharm Bull (Tokyo). 2006 April; 54(4):496-500).

Anti-type II collagen antibody (anti-CII Ab) is an autoantibody known to be present in RA patients (Firestein, Evolving concepts of rheumatoid arthritis. Nature 2003; 423:356-61). CAIA (collagen antibody-induced arthritis) is commonly used as an RA model for screening antirheumatic drugs because of its similarity with human RA. In the CAIA model, anti-CII Ab plays an important role; it induces arthritis in mice by passive transfer. An arthritis model using a mixture of 4 monoclonal anti-CII Abs has been established. This model can be prepared in constant yields by using various strains of mice, independent of MHC haplotypes. The data presented previously showed that IL-1beta concentration in irrigation fluid and relative expression level of IL-1beta mRNA in the synovium have potential as therapeutic markers in studying and treating CAIA (Chia et al., IL-1beta in irrigation fluid and mRNA expression in synovial tissue of the knee joint as therapeutic markers of inflammation in collagen antibody-induced arthritis. Dis Markers. 2009; 26(1):1-7). The previous study also showed that the matrix metalloproteinase (MMP)-9 (gelatinase B) mRNA level is a suitable marker for both acute and chronic stage, whereas IL-1beta is a marker only for the acute stage of the CAIA murine model (Chia et al., MMP-9 mRNA as a therapeutic marker in acute and chronic stages of arthritis induced by type II collagen antibody. J Formos Med Assoc. 2008 March; 107(3):245-52).

U.S. Pat. No. 7,109,232 discloses compounds and extracts from mycelium of *Antrodia cinnamomea* and the composition comprising the compound, which has anti-inflammation activity. But in its experiment, the inflammation model is induced by carrageenan, and only hind paw edema of rats are measured. The amelioration of systemic disease activity and the mechanism are still unknown.

U.S. Pat. No. 7,732,482 discloses a method of treating fibrosis in a mammal by the compounds from mycelium of *Antrodia cinnamomea*, wherein the fibrosis is mediated by TGF-β, and the TGF-β is associated with a disease state such as rheumatoid arthritis. But fibrosis can not be directly linked to rheumatoid arthritis since rheumatoid arthritis does not necessarily result in fibrosis. In addition, the mechanism of anti-disease activity of the compounds in rheumatoid arthritis is not disclosed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Balb/c mice were administered orally in all groups. The changes in the disease activating score of groups were recorded, and the data are represented as mean±SEM. (* $P<0.05$; ** $P<0.01$). The bars in day 3, day 7 and day 10 are respectively depicted as (left to right): Arthritis group, A group, B group, C group, D group, Water extract group, Ethanol extract group, and Mycelium group.

Figure 3:
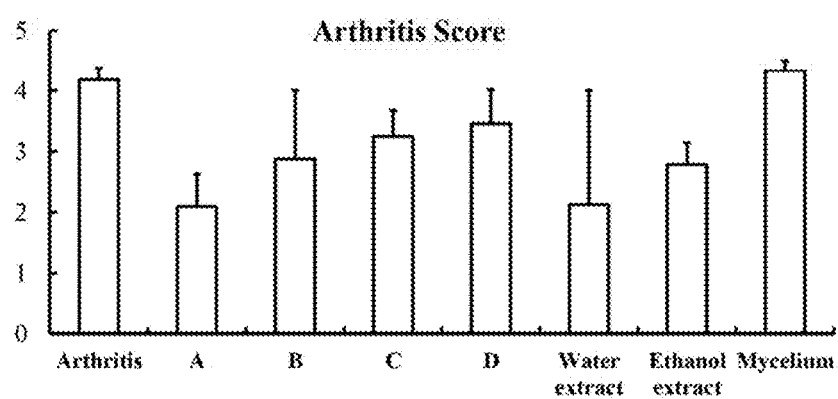

FIG. 3 shows pathological changes in treatment groups. There is a significant difference between arthritis group and other groups (* $P<0.05$; ** $P<0.01$).

Figure 4:
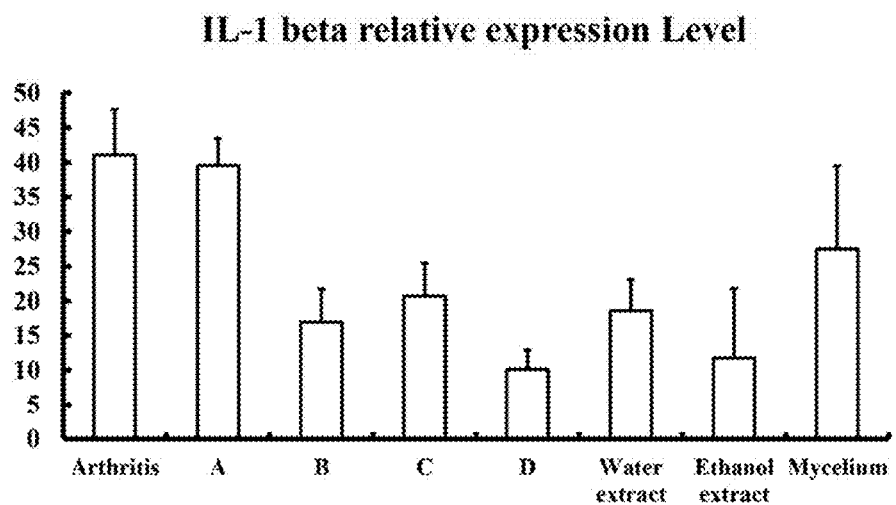

FIG. 4 shows relative expression levels of cytokines in footpad. There is a significant difference in IL-1β expression between groups (experiment performed in triplicate) (* $P<0.05$; ** $P<0.01$).

Figure 5:
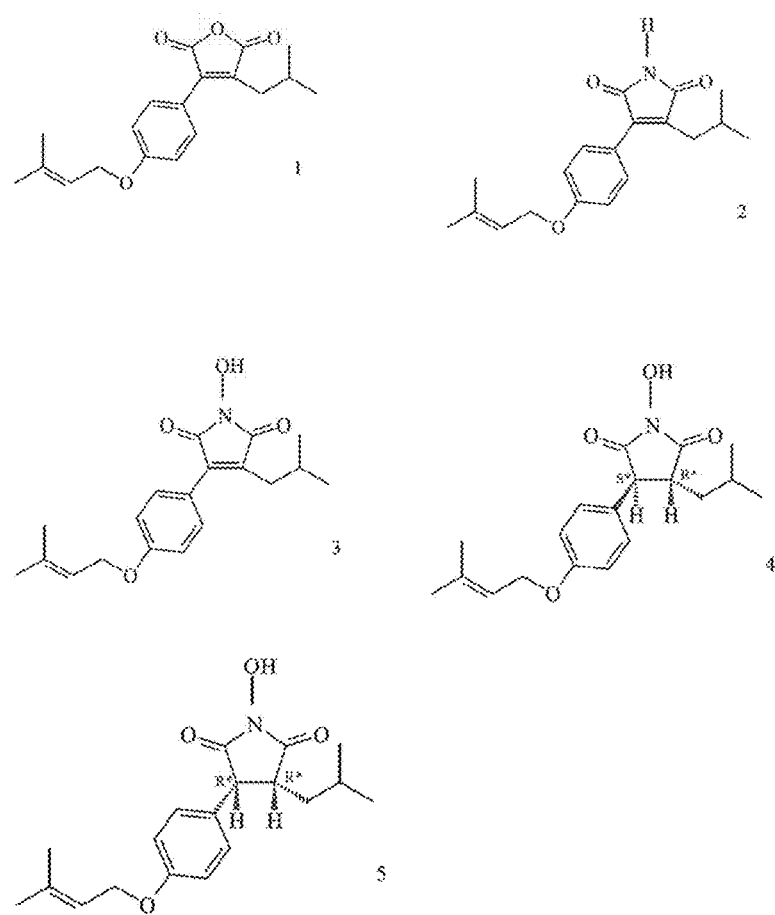

FIG. 5 shows the structure of compounds 1-5.

Figure 6A:
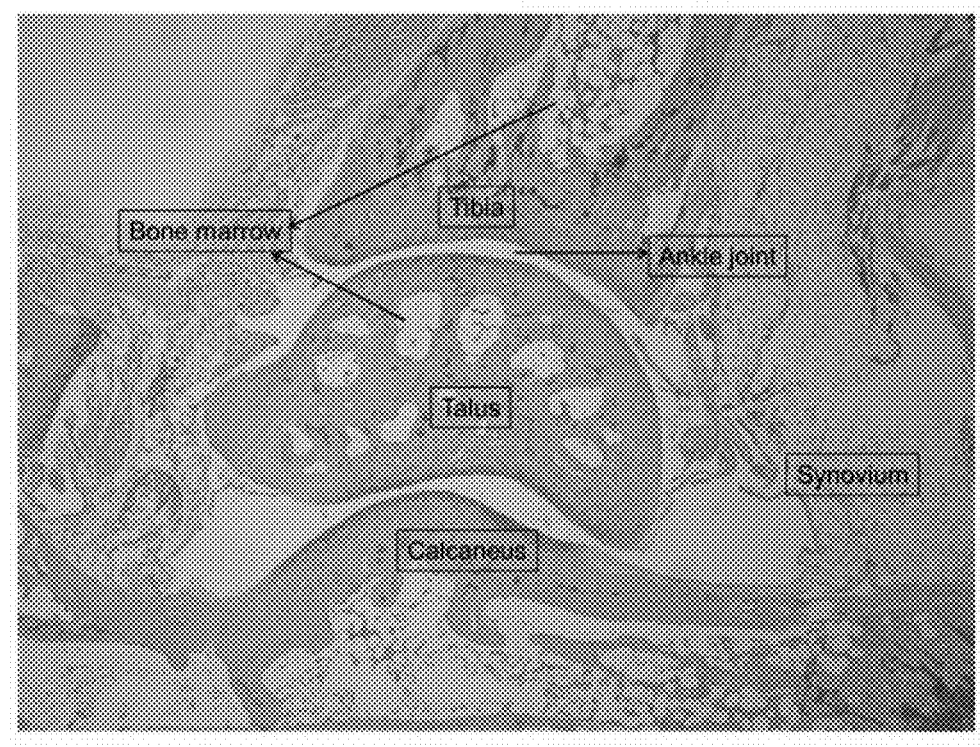
Figure 6B:
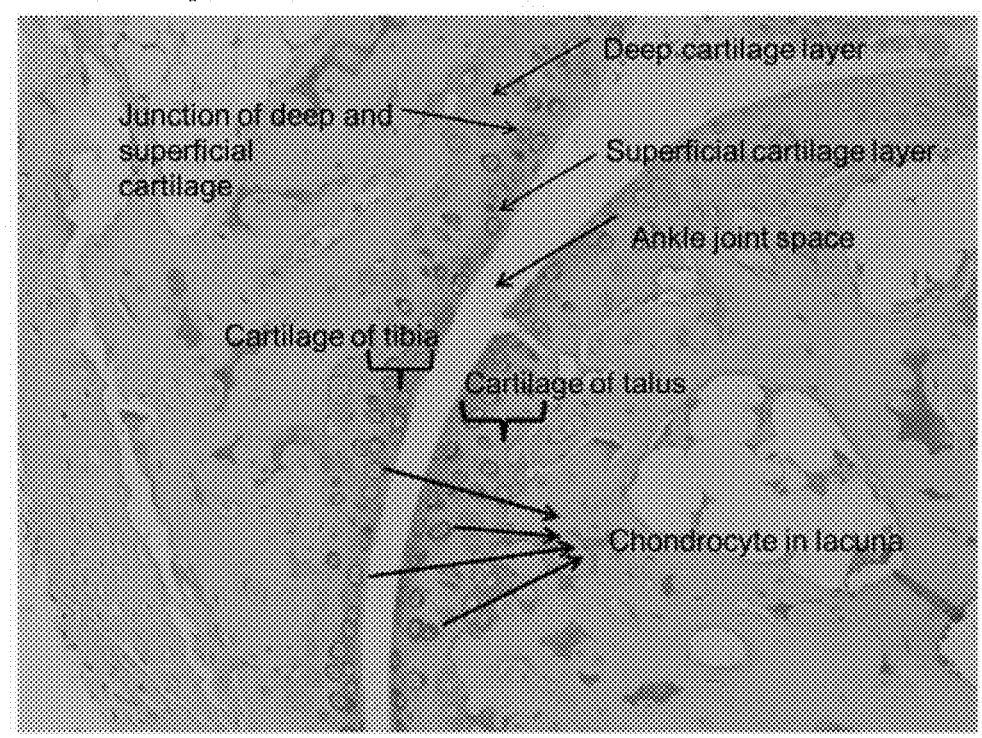
Figure 6C:
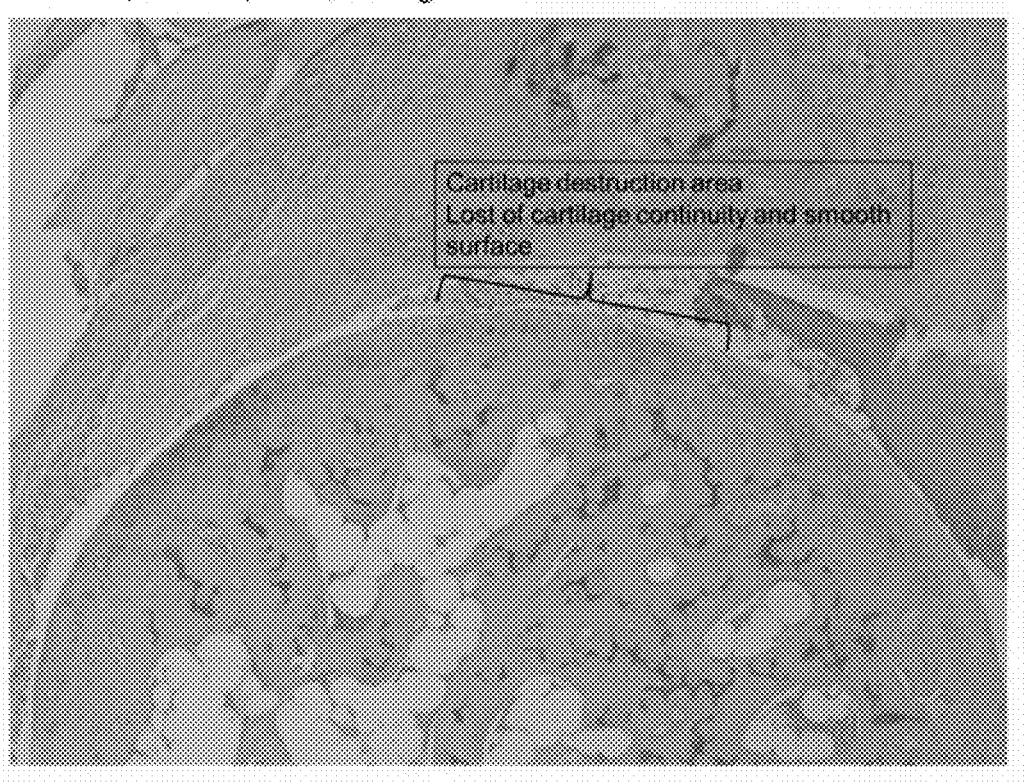
Figure 6D:
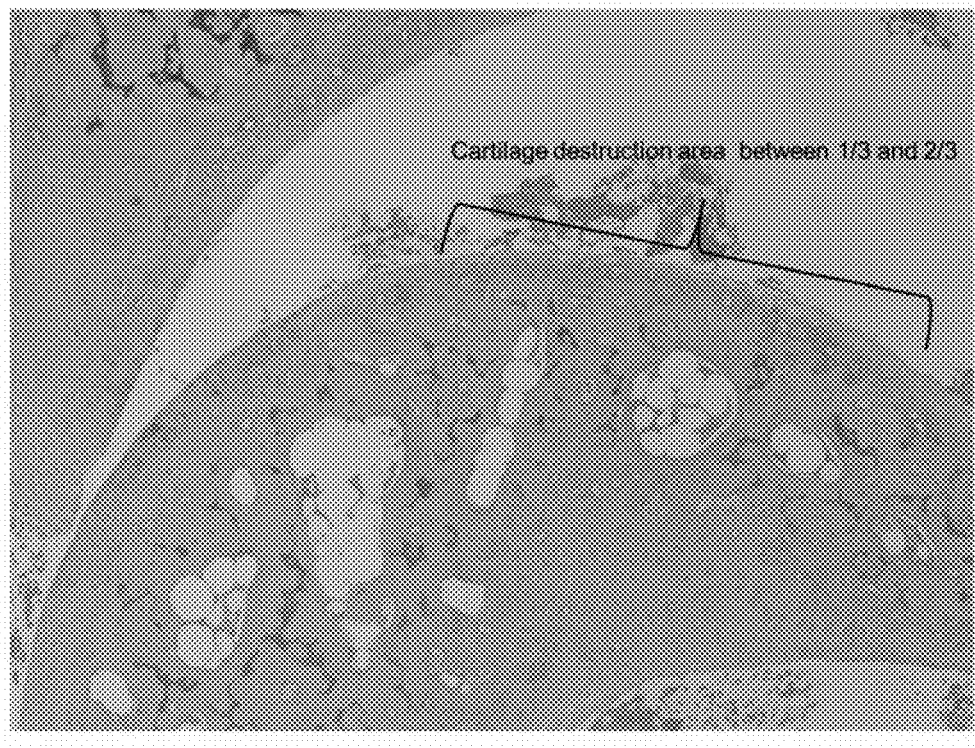
Figure 6E:
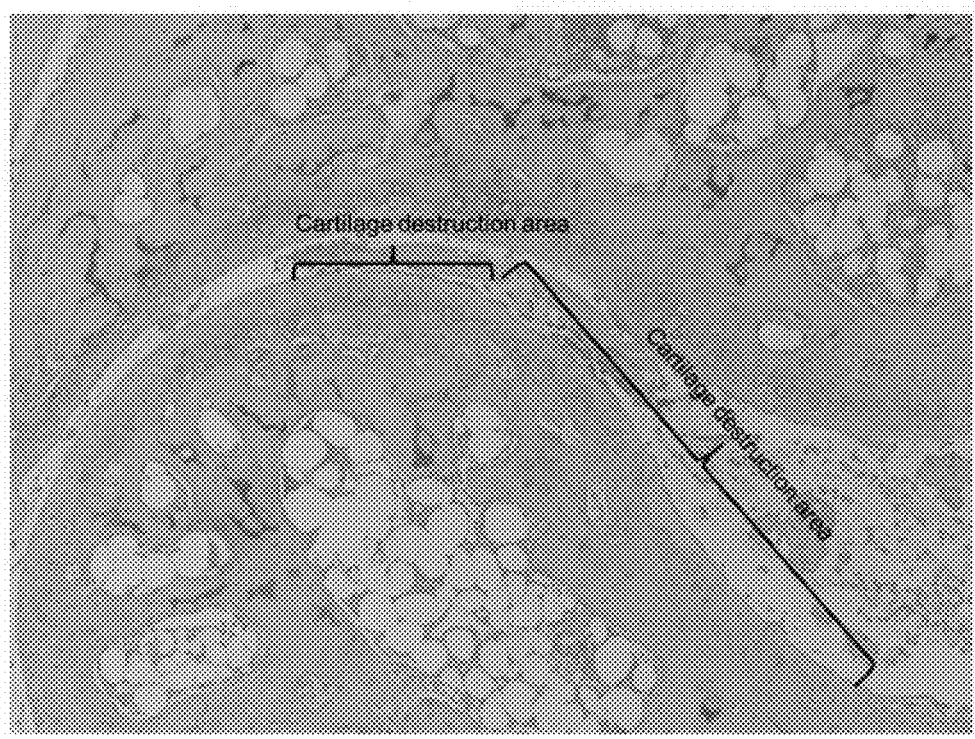

FIGS. 6A-6E show the histopathological scoring of cartilage destruction with FIGS. 6(A) (B) showing normal cartilage, score=0; (C) Score=1, cartilage destruction area<⅓; (D) Score=2, cartilage destruction area between ⅓ and ⅔; (E) Score=3, cartilage destruction area>⅔.

Figure 7:
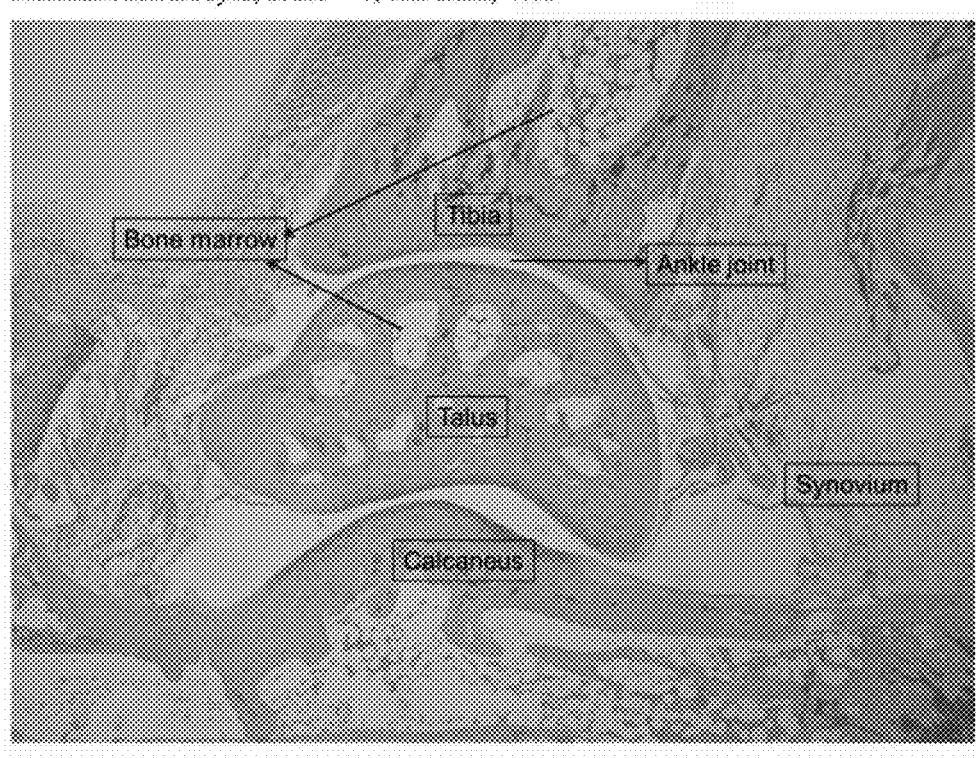

FIGS. 7A-7E show the histopathological scoring of chondrocyte death with FIG. 7(A) showing normal cartilage, score=0; (B) (C) Score=1, chondrocyte death area<⅓; (D) Score=2, chondrocyte death area between ⅓ and ⅔; (E) Score=3, chondrocyte death area>⅔.

Figure 8:
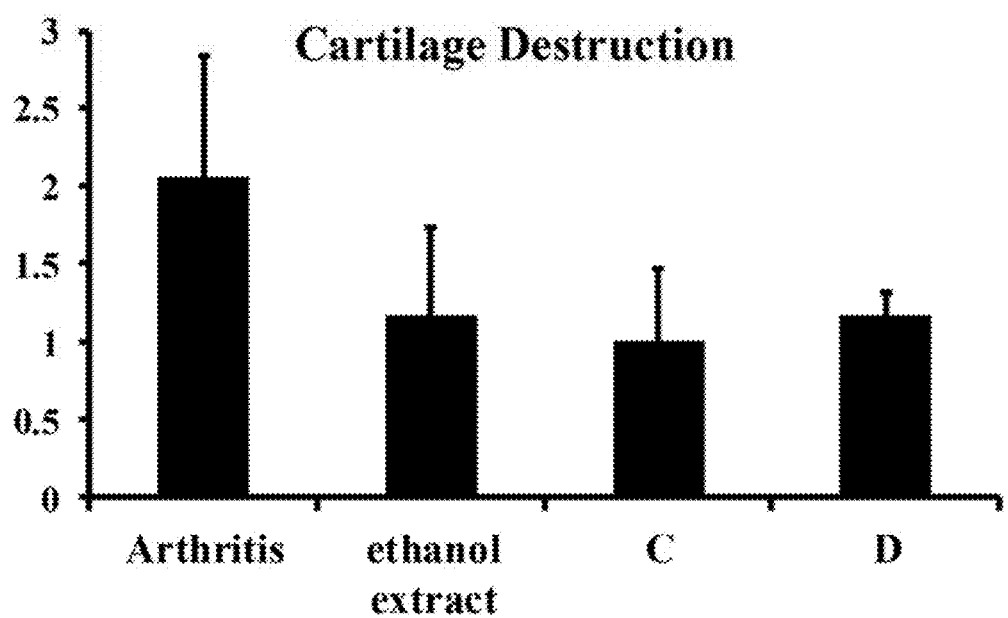

FIG. 8 shows cartilage destruction in treatment groups. There is a significant difference between arthritis group and other groups (* $P<0.05$).

Figure 9:
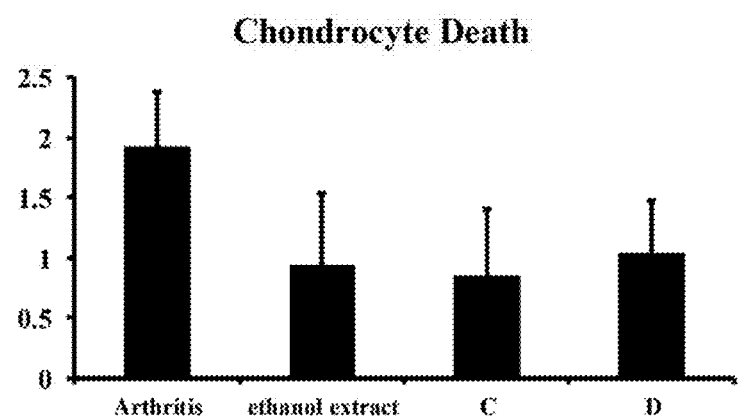

FIG. 9 shows chondrocyte death in treatment groups. There is a significant difference between arthritis group and other groups (* $P<0.05$; ** $P<0.01$).

SUMMARY OF THE INVENTION

The present invention relates to a method of preventing or ameliorating the symptoms of arthritis in a subject suffered from arthritis, comprising administrating to the subject an effective amount of an active component selected from
(a) a compound of formula (I),
(b) a mixture comprising water or organic solvent extract of mycelium of *Antrodia cinnamomea*, wherein the mixture comprises the compound of formula (I), and (c) a mycelium of *Antrodia cinnamomea*, wherein the mycelium comprises the compound of formula (I),

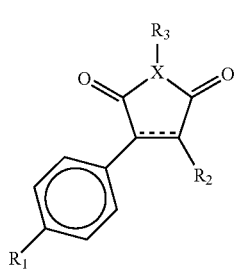

(I)

wherein
X is N or O;
$R_1$ is H, hydroxyl, $C_{1-10}$ alkyloxy, $C_{2-10}$ alkenyloxy, or $C_{2-10}$ alkynyloxy;
$R_2$ is H, hydroxyl, $C_{1-10}$ alkyl, $C_{2-10}$ alkenyl or $C_{2-10}$ alkynyl; and
$R_3$ is absent, H, hydroxyl, $C_{1-10}$ alkyl, $C_{2-10}$ alkenyl or $C_{2-10}$ alkynyl; provided that if X is O, $R_3$ is absent;

═══ denotes a single or double bond; provided that if ─── denotes a single bond, the compound has the formula:

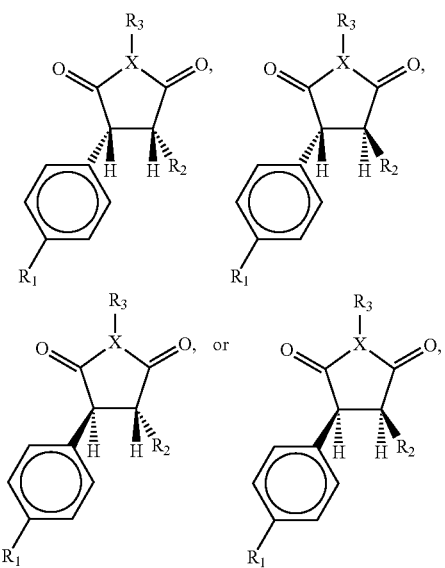

or a tautomer, stereoisomer, or pharmaceutically acceptable salt thereof.

The present invention also relates to a method of preventing or ameliorating cartilage destruction or chondrocyte death in a subject suffered from arthritis, comprising administrating to the subject an effective amount of an active component selected from
(a) a compound of formula (I),
(b) a mixture comprising water or organic solvent extract of mycelium of *Antrodia cinnamomea*, wherein the mixture comprises the compound of formula (I), and
(c) a mycelium of *Antrodia cinnamomea*, wherein the mycelium comprises the compound of formula (I),

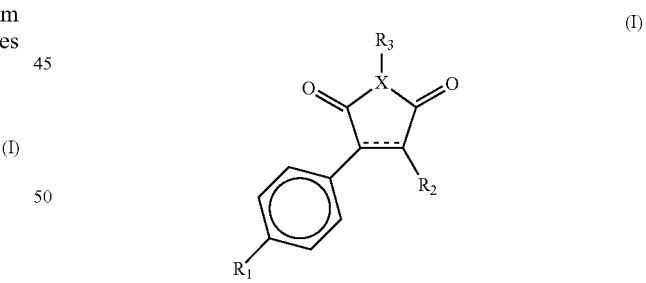

(I)

wherein
X is N or O;
$R_1$ is H, hydroxyl, $C_{1-10}$ alkyloxy, $C_{2-10}$ alkenyloxy, or $C_{2-10}$ alkynyloxy;
$R_2$ is H, hydroxyl, $C_{1-10}$ alkyl, $C_{2-10}$ alkenyl or $C_{2-10}$ alkynyl; and
$R_3$ is absent, H, hydroxyl, $C_{1-10}$ alkyl, $C_{2-10}$ alkenyl or $C_{2-10}$ alkynyl;
provided that if X is O, $R_3$ is absent;

═══ denotes a single or double bond; provided that if ─── denotes a single bond, the compound has the formula:

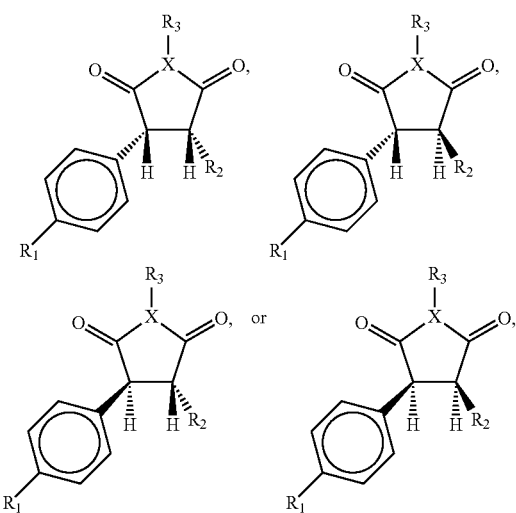

or a tautomer, stereoisomer, or pharmaceutically acceptable salt thereof.

DETAILED DESCRIPTION OF THE INVENTION

In the present invention, the ameliorative and preventive effect of compounds, extracts and mycelium from *Antrodia cinnamomea* in CAIA model is presented. The mechanism is associated with cytokine IL-1β. The cartilage destruction and chondrocyte death are also prevented in this model.

Thus, the present invention provides a method of preventing or ameliorating the symptoms of arthritis in a subject suffered from arthritis, comprising administrating to the subject an effective amount of an active component selected from (a) a compound of formula (I), (b) a mixture comprising water or organic solvent extract of mycelium of *Antrodia cinnamomea*, wherein the mixture comprises the compound of formula (I), and (c) a mycelium of *Antrodia cinnamomea*, wherein the mycelium comprises the compound of formula (I),

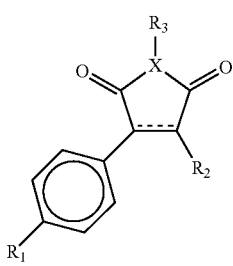

(I)

wherein

X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl; and $R_3$ is absent, H, hydroxyl, $C_{1-10}$ alkyl, $C_{2-10}$ alkenyl or $C_{2-10}$ alkynyl;

provided that if X is O, $R_3$ is absent;

≡ denotes a single or double bond; provided that if ≡ denotes a single bond, the compound has the formula:

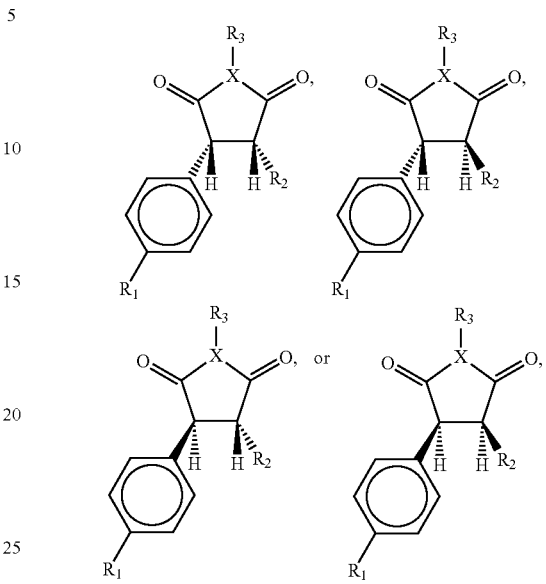

or a tautomer, stereoisomer, or pharmaceutically acceptable salt thereof.

The symptoms of arthritis described herein include generalized systemic disease activity such as swelling and redness of joints of limbs and edema.

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope- and halfchair-forms; and combinations thereof, hereinafter collectively referred to as "isomers" (or "isomeric forms").

If the compound is in crystalline form, it may exist in a number of different polymorphic forms.

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Unless otherwise specified, the compounds of the present invention include all such isomeric forms, including (wholly or partially) racemic and other mixtures thereof. Methods for the preparation (e.g., asymmetric synthesis) and separation (e.g., fractional crystallization and chromatographic means) of such isomeric forms are either known in the art or are readily obtained by adapting the methods taught herein, or known methods, in a known manner.

In a preferred embodiment, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

The organic solvent of the present invention includes but is not limited to alcohol (such as $CH_3OH$, $C_2H_5OH$, $C_3H_7OH$), ester (such as acetyl acetate), alkane (such as hexane) and halogenated alkane (such as $CH_3Cl$, $C_2H_2Cl_2$). The preferred organic solvent is ethanol or alcoholic solvent without causing any side effect of human. Preferably, the organic solvent is ethanol.

In a preferred embodiment, the mycelium of *Antrodia cinnamomea* is prepared by submerged liquid fermentation.

In a preferred embodiment, the arthritis is associated with IL-1β and the arthritis is rheumatoid arthritis or osteoarthritis. Preferably, the arthritis is rheumatoid arthritis.

In a preferred embodiment, the subject is a mammal. More preferably, the mammal is a human.

The present invention also provides a method of preventing or ameliorating cartilage destruction or chondrocyte death in a subject suffered from arthritis, comprising administrating to the subject an effective amount of an active component selected from (a) a compound of formula (I), (b) a mixture comprising water or organic solvent extract of mycelium of *Antrodia cinnamomea*, wherein the mixture comprises the compound of formula (I), and (c) a mycelium of *Antrodia cinnamomea*, wherein the mycelium comprises the compound of formula (I),

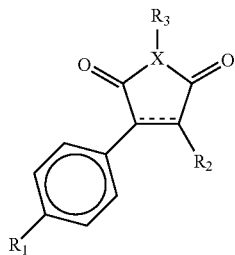

(I)

wherein

X is N or O;

$R_1$ is H, hydroxyl, $C_{1-10}$ alkyloxy, $C_{2-10}$ alkenyloxy, or $C_{2-10}$ alkynyloxy;

$R_2$ is H, hydroxyl, $C_{1-10}$ alkyl, $C_{2-10}$ alkenyl or $C_{2-10}$ alkynyl; and $R_3$ is absent, H, hydroxyl, $C_{1-10}$ alkyl, $C_{2-10}$ alkenyl or $C_{2-10}$ alkynyl;

provided that if X is O, $R_3$ is absent;

----- denotes a single or double bond; provided that if ----- denotes a single bond, the compound has the formula:

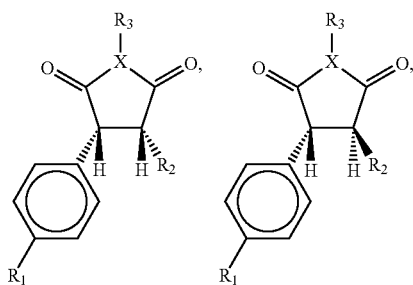

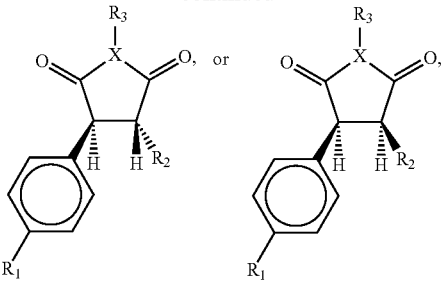

or a tautomer, stereoisomer, or pharmaceutically acceptable salt thereof.

In a preferred embodiment, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

The organic solvent of the present invention includes but is not limited to alcohol (such as $CH_3OH$, $C_2H_5OH$, $C_3H_7OH$), ester (such as acetyl acetate), alkane (such as hexane) and halogenated alkane (such as $CH_3Cl$, $C_2H_2Cl_2$). The preferred organic solvent is ethanol or alcoholic solvent without causing any side effect of human. Preferably, the organic solvent is ethanol.

In a preferred embodiment, the mycelium of *Antrodia cinnamomea* is prepared by submerged liquid fermentation.

In a preferred embodiment, the arthritis is associated with IL-1β and the arthritis is rheumatoid arthritis or osteoarthritis. Preferably, the arthritis is rheumatoid arthritis.

In a preferred embodiment, the subject is a mammal. More preferably, the mammal is a human.

The active component of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The active component of the invention may be in a form suitable for oral use, for example, as tablets, troches, lozenges, aqueous or oily suspensions, dispersible powders or granules, emulsions, hard or soft capsules, or syrups or elixirs. Active component intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, active component for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The active component may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Active component contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

Those of skill in the art recognize that the mixture described herein can be delivered in a variety of ways, such as, for example, orally, intravenously, subcutaneously, parenterally, rectally, by inhalation, and the like.

Since individual subjects may present a wide variation in severity of symptoms and each drug has its unique therapeutic characteristics, the precise mode of administration and dosage employed for each subject is left to the discretion of the practitioner.

EXAMPLES

The examples below are non-limiting and are merely representative of various aspects and features of the present invention.

Example 1

Material and Methods

1. Mice

Male BALB/cByJNarl (BALB/c) mice were purchased at age six weeks from National Laboratory Animal Center (Taiwan) and subsequently bred and maintained under specific pathogen-free conditions in the Laboratory Animal Center of National Defense Medical Center (Taipei, Taiwan).

2. Sample Preparation

Five New Maleic and Succinic Acid Derivatives

Hepasim (major active compound representing the maleic and succinic acid derivatives (cyclic imides) isolated by Dr. Hattori) were isolated from the mycelium of *Antrodia cinnamomea* (provided by Simpson Biotech Co., Ltd.).

Powdered mycelia of *Antrodia cinnamomea* (60 g), from Simpson Biotech Co., Ltd., Taiwan, October 2001, were extracted with $CHCl_3$ (×3) for 3 h under reflux. The $CHCl_3$ extract (5.3 g) was chromatographed on silica gel eluted with n-hexane-acetone (19:1-14:6) and $CHCl_3$-MeOH (1:1) to give nine fractions (Fr. 1-9). Fraction 2 was chromatographed on silica gel to give compound 1 (8.7 mg). Fraction 4 was chromatographed on normal and reversed phase silica gel to give compound 2 (13.6 mg). Fraction 6 gave compound 3 (14.6 mg) by combination of normal and reversed-phase silica gel column chromatography. Fraction 7 yielded a mixture of compound 4 and compound 5 (4:1) by column chromatography. The mixture of compound 4 and compound 5 was subsequently separated by preparative HPLC [column: Tosoh TSK-gel ODS-80TM (21.5×300 mm), mobile phase: $CH_3OH$—$H_2O$ containing 0.1% TFA (70:30)]. The structure of compounds 1-5 were shown in FIG. 5. Compound 1 is 3-isobutyl-4-[4-(3-methyl-2-butenyloxy)phenyl]furan-2,5-dione, compound 2 is 3-isobutyl-4-[4-(3-methyl-2-butenyloxy)phenyl]-1H-pyrrol-2,5-dione, compound 3 is 3-isobutyl-4-[4-(3-methyl-2-butenyloxy)phenyl]-1H-pyrrol-1-ol-2,5-dione, compound 4 is 3R*,4S*-1-hydroxy-3-isobutyl-4-[4-(3-methyl-2-butenyloxy)phenyl]pyrrolidine-2,5-dione, and compound 5 is 3R*,4R*-1-hydroxy-3-isobutyl-4-[4-(3-methyl-2-butenyloxy)phenyl]pyrrolidine-2,5-dione. Detailed description of these compounds was disclosed in U.S. Pat. No. 7,109,232. In the following example, A group refers to the group administering compound 1; B group refers to the group administering compound 2; C group refers to the group administering compound 3; and D group refers to the group administering compound 4.

Water Extract from Mycelium of *Antrodia cinnamomea*

Fermentated mycelium of *Antrodia camphorata* was added in 85° C. hot water (mycelium:water=1:5 by weight) and evenly stirred 4 hours. Then the reaction mixture was cooled to 30° C. and liquid was separated by using a separator. The liquid was concentrated by vacuum evaporation to obtain the water extract.

Ethanol Extract from Mycelium of *Antrodia cinnamomea*

Fermentated mycelium of *Antrodia camphorata* was added in ethanol (mycelium:ethanol=1:5 by weight), heated to 60-65° C. and stirred. Then the reaction mixture was cooled to 40° C. and liquid was separated by using a separator. The liquid was concentrated by vacuum evaporation to obtain the ethanol extract.

Mycelium of *Antrodia cinnamomea*

The mycelium of *Antrodia cinnamomea* a is previously prepared according to submerged liquid fermentation such as T. L. M. Stamford et al., Food Science "Protein enrichment of cashew wastes for animal feeds" from http://www.unu.edu/unupress/food/8F101e/8F101E0b.htm.

3. Induction of Arthritis in Mice

An arthritogenic monoclonal antibody (mAb) cocktail and lipopolysaccharide (LPS) were purchased from Immuno-Biological Laboratories (Hamburg, Germany). Arthritis was induced by the method of Terato et al. (Terato et al., Induction of arthritis with monoclonal antibodies to collagen. *J Immunol.* 1992 Apr. 1; 148(7):2103-8), using an arthritogenic mAb cocktail that contained four mAbs (F10, A2, D8, and D1) in equal amounts and using LPS as adjuvant. Three clones (F10, A2, and D8) were of type IgG2a, and one clone (D1) was type IgG2b. To induce arthritis, each mouse was injected intravenously with 2 mg of anti-CII mAbs followed by an intraperitoneal injection of 50 μg (BALB/c background) LPS (*Escherichia coli* 0111: B4) three days later. Isotype IgG (anti-mouse IgG, 2 mg, Jackson Lab.) supplied with LPS and only LPS induction groups were applied in same condition.

4. Clinical Assessment of Arthritis

Arthritis development was monitored in the four limbs using a macroscopic scoring system. Briefly, one point was given for each swollen or red toe; one point for each swollen joint (metatarsal-phalangeal joints, metacarpal-phalangeal joints, proximal interphalangeal joints, and distal interphalangeal joints); and five points for a swollen ankle (maximum score=15 per limb and 60 per mouse) (Nandakumar et al., Collagen type II (CII)-specific antibodies induce arthritis in the absence of T or B cells but the arthritis progression is enhanced by CII-reactive T cells. Arthritis Res. Ther. 6 (2004), R544-R550). The mice were examined on days 0, 3, 7, 10 and 14 after the mAb injection. The thickness of each paw was measured in a noncontact manner using a Simplified Geometry Measurement System (Advanced Design Research Technology Co., Ltd). Images of the paws of each mouse were recorded three times (Chia et al., A noncontact footpad thickness assay to evaluate rheumatoid disease. Rheumatol Int. 2010 February; 30(4):547-50). One trained researcher who was blinded to group treatments evaluated the image data independently.

5. Histological Examination

The ankle joints were fixed in 10% formalin, decalcified, trimmed, and embedded. Sections were prepared from the tissue blocks and stained with hematoxylin and eosin. Histopathological scoring was performed as described below. Ankle joints of arthritic mice were given arthritis scores of 0, 1, 2, 3, 4, and 5 to describe the arthritis according to the following criteria: 0, normal; 1, minimal infiltration of polymorphonuclear leukocytes in the periarticular area; 2, mild infiltration; 3, moderate infiltration; 4, marked infiltration; and 5, severe infiltration (Doherty, 2001. Risk factors for progression of knee osteoarthritis. Lancet 358:775-6). Three independent observers scored each slide, and the average score was used.

6. RNA Isolation, Reverse Transcription, and Quantitative Polymerase Chain Reaction (PCR)

Total RNA was isolated using the Trizol method. Footpad tissues were homogenized in Trizol lysis buffer followed by chloroform extraction (Life Technologies). The RNA was eluted with 20 μl of RNase-free water. All RNA was quantified by spectrophotometer, and the optical density (OD) 260/280 nm ratio was determined. For cDNA synthesis, 5 μg total RNA was reverse transcribed at 50° C. for 60 min using 200 units of Superscript III reverse transcriptase (Invitrogen). The primer sequence was as follows: IL1-β, forward primer (5'-CCAGCAGGTTATCATCATCATCC), reverse primer (5'-CTCGCAGCAGCACATCAAC); and GAPDH, forward primer (5'-TGGCAAAGTGGAGATTGT-TGCC), reverse primer (5'-AAGATGGTGATGGGCTTC-CCG). The SYBR Green master mix kit (Bio-Rad) was used for all reactions with real-time PCR. Briefly, PCR was performed as follows: 94° C. for 2 min followed by 40 cycles of denaturation; annealing; and extension at 94° C. for 15 s, 64° C. for 30 s, and 72° C. for 45 s; and final extension at 72° C. for 10 min. The PCR reaction was performed in triplicate for each sample for all the products and for the GAPDH control. Ratios for each product relative to GAPDH mRNA were calculated for each sample. The data presented are expressed as the fold-increase or fold-decrease in mRNA level. For all real-time PCR assays, the products were run out on a gel to confirm the presence of a single band.

7. Statistical Analysis

Data were analyzed by the Mann-Whitney U test and were expressed as mean±SEM. A P value <0.05 was considered significant.

Results

Figure 1:
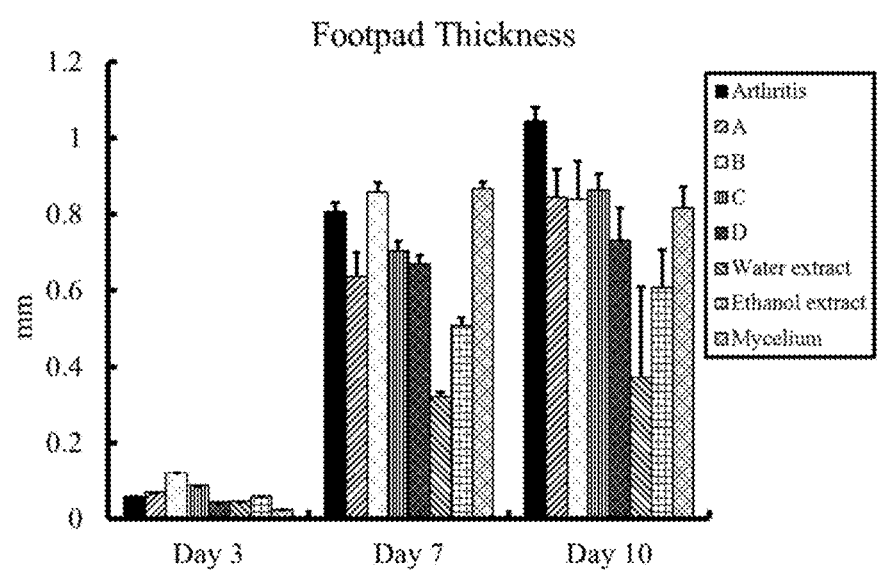
FIG. 1 shows systemic disease activity reflected changes in footpad thickness in the acute stage of CAIA. Balb/c mice were administered orally in all groups. The relative changes in the footpad thickness of groups were recorded, and the data are represented as mean±SEM. (* P<0.05; ** P<0.01). The bars in day 3, day 7 and day 10 are respectively depicted as (left to right): Arthritis group, A group, B group, C group, D group, Water extract group, Ethanol extract group, and Mycelium group.

1. Systemic Disease Activity Reflected Changes in Footpad Thickness in the Acute Stage of CAIA In stimulation of acute arthritis exacerbation in CAIA, footpad thickness dramatically increased from days 7 to 10 (FIG. 1) as compared to the baseline; the footpad thickness on day 7 showed an average increase of 0.806±0.0368 mm (Arthritis group) and that on day 10 showed an average increase of 1.0446±0.0369 mm (n=13). The footpad thickness and P value on day 10 in groups were showed: A group: 0.840±0.139 (n=3, P=0.0201); B group: 0.837±0.177 (n=3, P=0.0446); C group: 0.8605±0.098 (n=7, P=0.0446); D group: 0.729±0.114 (n=4, P=0.009); water extract group: 0.369±0.365 (n=3, P=0.0201); ethanol extract group: 0.6035±0.131 (n=9, P=0.003); mycelium group: 0.813±0.083 (n=3, P=0.0078) on day 10 (FIG. 1). However, there was also significant difference in A group, C group, water extract group and ethanol extract group on day 7. In each group, the subjects were given the sample once daily (300 ml/Kg) since day 0 to day 9 via oral intake and the subjects was administrated before the antibody and LPS injection.

Figure 2:
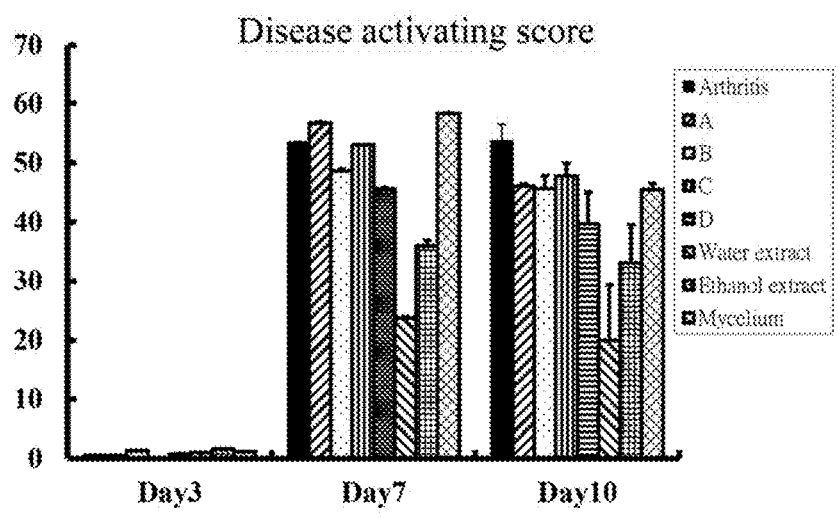
FIG. 2 shows systemic disease activity reflected changes in disease activating score in the acute stage of CAIA.

2. Systemic Disease Activity Reflected Changes in Disease Activity Score in the Acute Stage of CAIA The arthritis and P value on day 10 in groups were showed: Arthritis group: 53.71±2.763 (n=8); A group: 46.0±2.537 (n=3, P=0.0206); B group: 45.58±4.818 (n=3, P=0.0319); C group: 47.718±3.581 (n=8, P=0.0353); D group: 39.687±5.238 (n=4, P=0.0104); water extract group: 20.0±13.769 (n=3, P<0.001); ethanol extract group: 33.1±5.724 (n=10, P=0.0052); mycelium group: 45.41±8.05 (n=3, P=0.038) on day 10. (FIG. 2) However, there was also significant difference in D group, water extract group and ethanol extract group on day 7.

3. The Amelioration of Arthritis Score

The arthritis score was reduced in treatment groups. The experimental period was unremarkable with no infections. The ankle joint were harvested on day 10. The arthritis score of groups were showed: Arthritis group: 4.178±0.2023 (n=7); A group: 2.093±0.541 (n=4, P=0.0035); B group:

42.875±1.125 (n=2, P=0.0358); C group: 3.25±0.421 (n=8, P=0.0234); D group: 3.458±0.559 (n=3, P=0.0428); water extract group: 2.125±1.875 (n=2, P<0.0035); ethanol extract group: 2.78±0.362 (n=4, P=0.0358); mycelium group: 4.33±0.167 (n=3, P=0.123) on day 10. (FIG. 3)

4. The Relative Expression Levels of Cytokines IL-1β

The relative expression levels of cytokines IL-1β was reduced in treatment groups. The relative expression levels of IL-1β were showed: Arthritis group: 41.13±6.465 (n=8); A group: 39.61±3.849 (n=3, P=0.1678); B group: 16.873±4.82 (n=3, P=0.0062); C group: 20.714±4.751 (n=8, P=0.0039); D group: 10.141±2.765 (n=4, P=0.0016); water extract group: 11.69±10.116 (n=3, P<0.0106); ethanol extract group: 18.636±4.45 (n=10, P=0.0029); mycelium group: 27.505±11.987 (n=3, P=0.0768) on day 10. (FIG. 4)

Example 2

Material and Methods

The ankle joints were fixed in 10% formalin, decalcified, trimmed, and embedded. Sections were prepared from the tissue blocks and stained with hematoxylin and eosin. Histopathological scoring was performed as described below. Ankle joints of arthritic mice were given cartilage destruction scores of 0, 1, 2, and 3 to describe the cartilage destruction according to the following criteria: 0, normal (FIGS. 6A, 6B); 1, mild cartilage surface fissure or cartilage loss (around less than ⅓ cartilage surface in all sections, FIG. 6C); 2, moderate cartilage surface fissure or cartilage loss (between ⅓ to ⅔ area, FIG. 6D); 3, severe cartilage destruction (more than ⅔, FIG. 6E). Two independent observers scored each slide, and the average score was used.

Figure 7B:
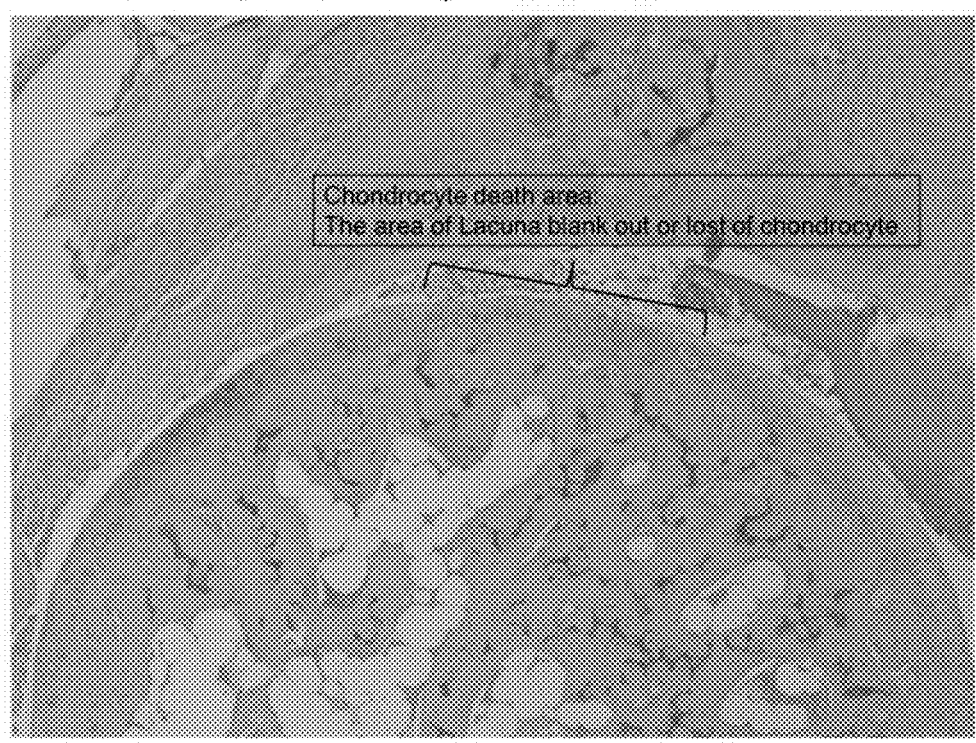
Figure 7C:
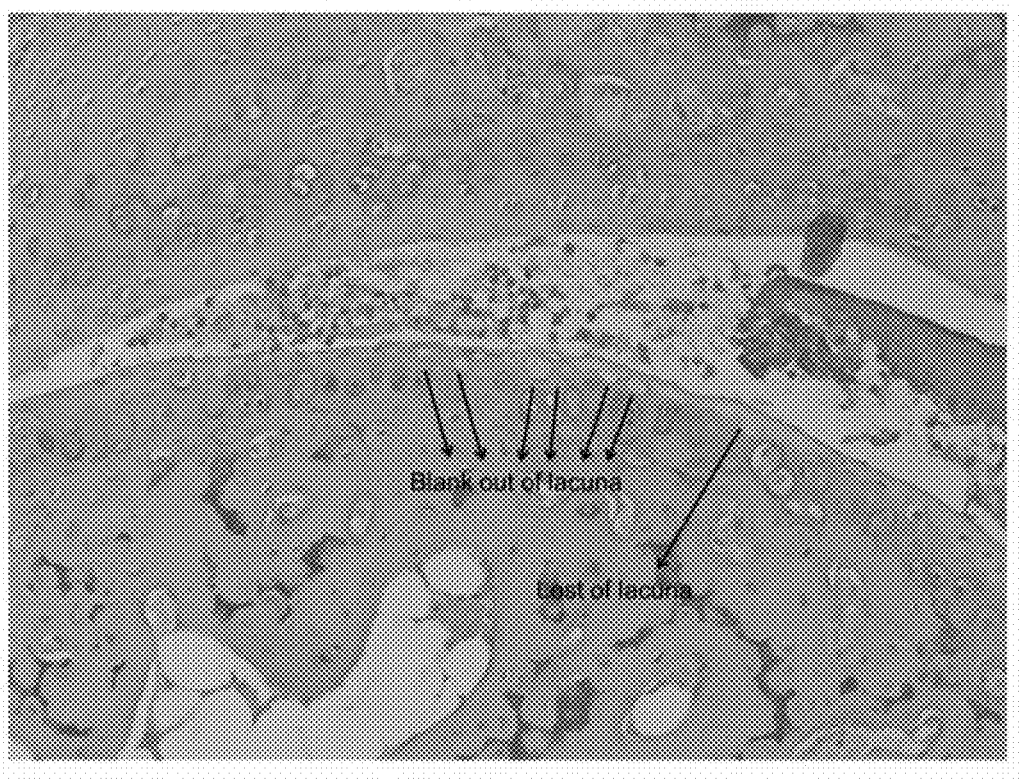
Figure 7D:
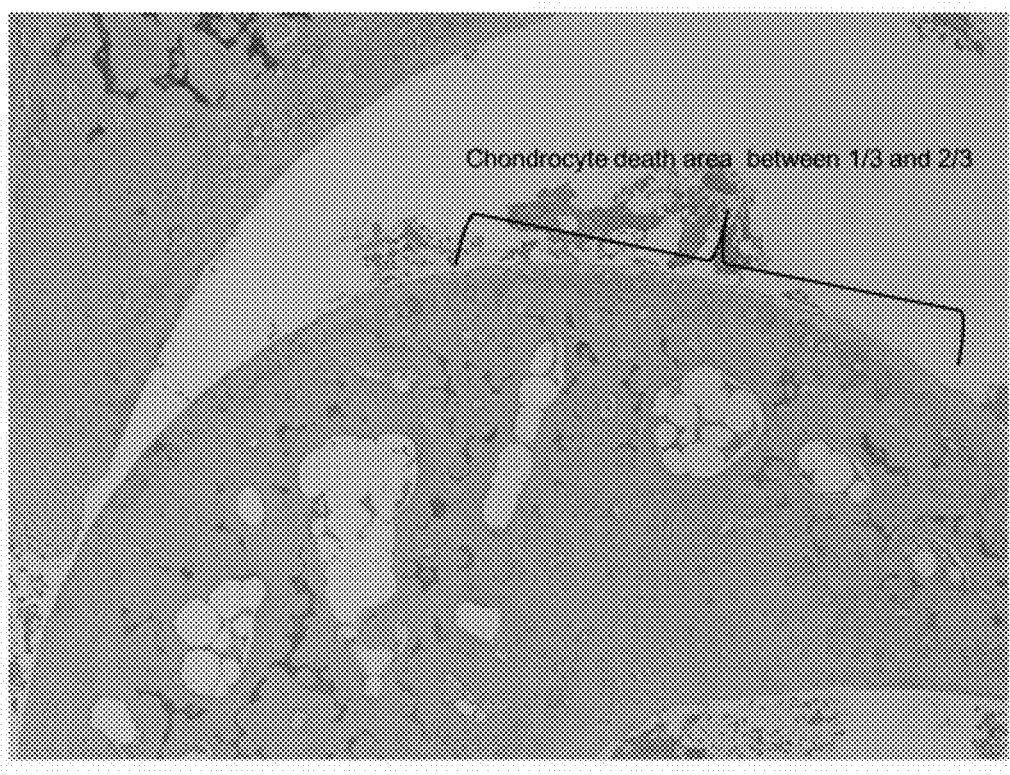
Figure 7E:
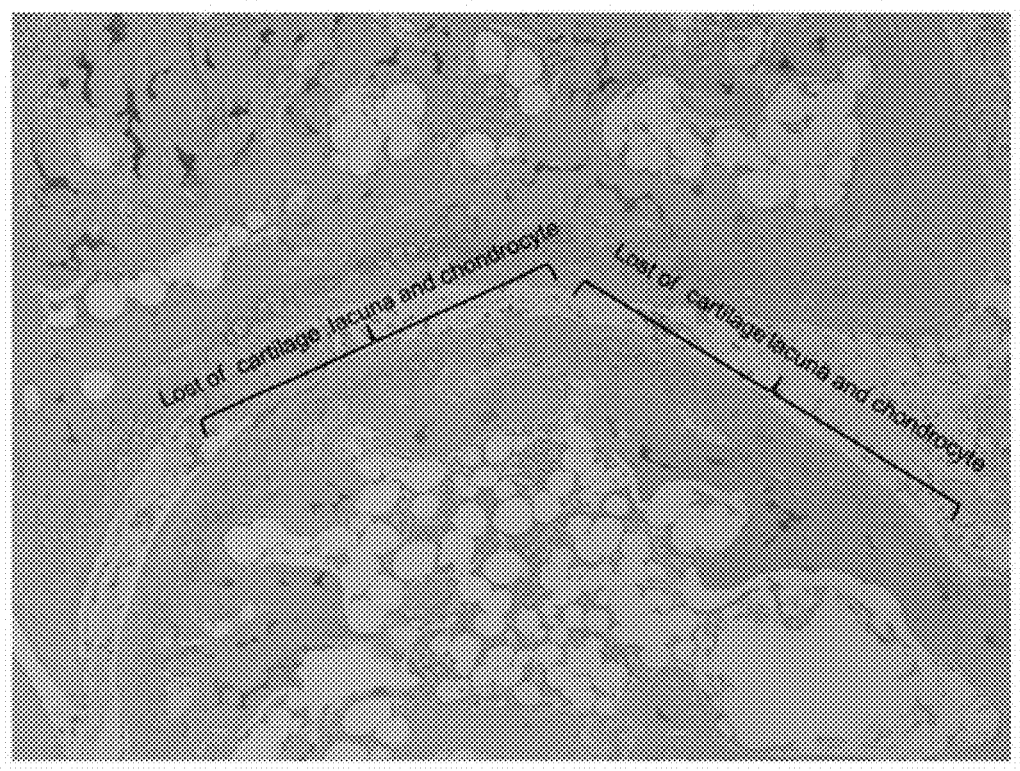

Ankle joints of arthritic mice were given chondrocyte death scores of 0, 1, 2, and 3 to describe the chondrocyte death according to the following criteria: 0, normal (FIG. 7A); 1, mild chondrocyte death (around less than ⅓ chondrocyte death in cartilage of all sections, FIGS. 7B, 7C); 2, moderate chondrocyte death (between ⅓ to ⅔ area chondrocyte death in the cartilage, FIG. 7D); 3, severe chondrocyte death (more than ⅔ chondrocyte death in the cartilage, FIG. 7E). Two independent observers scored each slide, and the average score was used.

Statistical Analysis

Data were analyzed by the t test and are expressed as mean±SD. A P value<0.05 was considered significant.

Results

1. The cartilage Destruction Score in Treatment of C, D, and Ethanol Extract Groups The cartilage destruction score was reduced in C, D, and ethanol extract treatment groups. The experimental period was unremarkable with no infections. The ankle joint were harvested on day 10. the cartilage destruction score of groups were showed: arthritis group: 2.063±0.776 (n=8); C group: 1.000±0.467 (n=5, p=0.010); D group: 1.167±0.144 (n=3, p=0.014); ethanol extract group: 1.167±0.573 (n=9, p=0.019). (FIG. 8)

2. The Chondrocyte Death Score in Treatment of C, D, and Ethanol Extract Groups

The chondrocyte death score was reduced in C, D, and ethanol extract treatment groups. The experimental period was unremarkable with no infections. The ankle joint were harvested on day 10. The chondrocyte death score of groups were showed: arthritis group: 1.929±0.450 (n=7); C group: 0.58±0.555 (n=5, p=0.008); D group: 1.042±0.439 (n=3, p=0.045); ethanol extract group: 0.944±0.594 (n=8, p=0.007). (FIG. 9)

One skilled in the art readily appreciates that the present invention is well adapted to carry out the objects and obtain the ends and advantages mentioned, as well as those inherent therein. The compound, mixture, mycelium, processes and methods for producing them and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating a human suffering from osteoarthritis or rheumatoid arthritis, comprising administering a therapeutically effective amount of an extract of mycelium of *Antrodia cinnamomea* which is prepared by submerged liquid fermentation to said human suffering from osteoarthritis or rheumatoid arthritis to effectively treat the osteoarthritis or rheumatoid arthritis in said human, wherein said extract of mycelium of *Antrodia cinnamomea* comprises a compound of formula I,

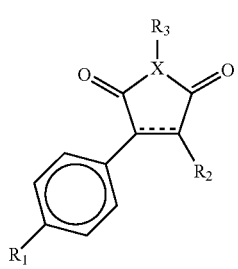

(I)

wherein
X is N or O;
$R_1$ is H, hydroxyl, $C_{1-10}$ alkyloxy, $C_{2-10}$ alkenyloxy, or $C_{2-10}$ alkynyloxy;
$R_2$ is H, hydroxyl, $C_{1-10}$ alkyl, $C_{2-10}$ alkenyl or $C_{2-10}$ alkynyl; and
$R_3$ is absent, H, hydroxyl, $C_{1-10}$ alkyl, $C_{2-10}$ alkenyl or $C_{2-10}$ alkynyl;

provided that if X is O, $R_3$ is absent;

═══ denotes a single or double bond; provided that if ─── denotes a single bond, the compound has the formula:

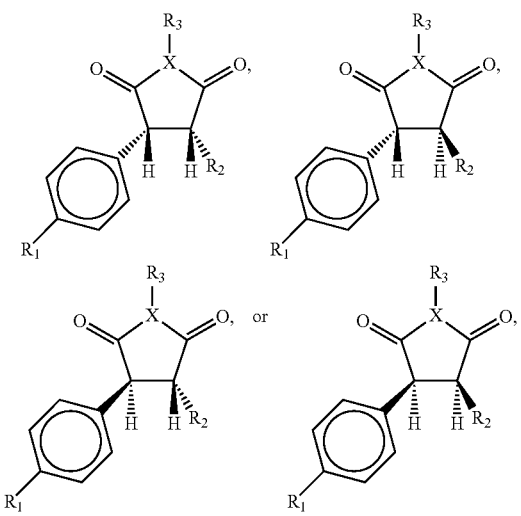

or a tautomer, stereoisomer, or pharmaceutically acceptable salt thereof.

2. The method of claim 1, wherein the compound is 3-isobutyl-4-[4-(3-methyl-2-butenyloxy)phenyl]furan-2,5-dione, 3-isobutyl-4-[4-(3-methyl-2-butenyloxy)phenyl]-1H- pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R*,4R*-1-hydroxy-3-isobutyl-4-[4-(3-methyl-2-butenyloxy)phenyl]pyrrolidine-2,5-dione.

3. The method of claim 1, which reduces IL-1β expression.

* * * * *